(12) United States Patent
Kluwe

(10) Patent No.: US 6,660,477 B2
(45) Date of Patent: Dec. 9, 2003

(54) METHOD FOR THE DETERMINATION OF DATA FOR THE PREPARATION OF THE DIAGNOSIS OF PHAKOMATOSIS

(75) Inventor: Lan Kluwe, Hamburg (DE)

(73) Assignee: Von Recklinghausen Gesellschaft E.V., Hamburg (DE)

(*) Notice: Subject to any disclaimer, the term of this patent is extended or adjusted under 35 U.S.C. 154(b) by 0 days.

(21) Appl. No.: 09/893,237

(22) Filed: Jun. 27, 2001

(65) Prior Publication Data

US 2001/0055770 A1 Dec. 27, 2001

(30) Foreign Application Priority Data

Jun. 27, 2000 (EP) .............................................. 00113607

(51) Int. Cl.⁷ ............................ C12Q 1/68; C12P 19/34; C07H 21/04
(52) U.S. Cl. ......................... 435/6; 435/91.2; 536/23.1
(58) Field of Search .................... 435/6, 91.2; 536/23.1

(56) References Cited

U.S. PATENT DOCUMENTS

| | | | |
|---|---|---|---|
| 5,605,799 A | 2/1997 | White et al. | |
| 5,952,170 A | 9/1999 | Stroun et al. | |
| 6,077,685 A | * 6/2000 | Trofatter et al. | ........... 435/69.1 |

OTHER PUBLICATIONS

Baser et al. Presymptomatic diagnosis of neurofibromatosis 2 using linked genetic markers, neuroimaging, andocular examinations. Neurology vol. 47:1269–1277, 1996.*
Ueki et al. Tight association of loss of merlin expressino with loss heterozygosity at chromosome 22q in sporadic meningiomas. Cancer Res. vol. 59:5995–5998, Dec. 1999.*
Sainz et al. Loss of alleles in vestibular schwannomas Arch. Otolaryngol. Head Neck Surg. vol. 119:1285–1288, 1993.*
Ng et al. Combined molecular genetic studies of chromosome 22q and the neurofibromatosis type 2 gene in central nervous system tumors. Neurosurgery vol. 37(4):764–773, 1995.*
Jacoby et al. Molecular analysis of the NF2 tumor–suppressor gene in schwannomatosis. Am. J. Hum. Genet. Vo. 61:1293–1297, 1997.*
Kluwe et al. The parental origin of new mutations in neurofibromatosis 2. Neurogenetics vol. 3:17–24, 2000.*
Valero et al. Linkage disequilibrium between four intragenic polymorphic microsatellites of the NF1 gene and its implications for genetic counselling. J. Mol. Genet. vol. 3:590–593, 1996.*
Irving et al. Molecular genetic analysis of the mechanism of tumorigenesis in acoustic neuroma. Arch. Otolaryngol. Head Neck Surg. vol. 119:1222–1228, 1993.*
The 9$^{th}$ European Neurofibromatosis Meeting Program, Apr. 6–8, 2001, Venice, Italy.

L. Kluwe, et al., "Presymptomatic diagnosis for children of sporadic neurofibromatosis 2 patients: A method based on tumor analysis," *Genetics in Medicine*, 4(1), pp. 1–4 (2001).
M.E. Baser, et al., "Presymptomatic diagnosis of neurofibromatosis 2 using linked genetic markers, neuroimaging, and ocular examinations," *Neurology*, pp. 1269–1277 (1966).
L. Kluwe, et al., "Mosaicism in sporadic neurogibromatosis 2 patients," *Human Molecular Genetics*, 7(13), pp. 2051–2055 (1998).
L. Kluwe, et al., "Allelic Loss of the NF1 Gene in NF1–Associated Plexiform Neurofibromas," *Cancer Genet Cytogenet*, 113, pp. 65–69 (1999).
L. Kluwe, "Loss of NF1 Allele in Schwann Cells But Not in Fibroblasts Derived From an NF1–associated Neurofibroma," *Genes, Chromosomes & Cancer* 24:283–285 (1999).
L. Kluwe, et al., "The parental origin of new mutations in neurofibromatosis 2," *Neurogenetics*, 3, pp. 17–24 (2000).
D.R. Lohmann, et al., "Molecular analysis and predictive testing in retinoblastoma," *Ophthalmic Genetics*, 16(4), pp. 135–142 (1995).
V–F Mautner, et al., "Neurofibromatosis versus schwannomatosis", *Fortschritte der Neurologie Psychiatrie*, 66, pp. 271–277 (1988). [Abstract only—from BIOSIS Online, Biosciences Information Services, Philadelphia, PA].
P. Riva, et al., "Characterization of a cytogenic 17q11.2 deletion in an NF1 patient with a contiguous gene syndrome," *Hum Genet*, 98, pp. 646–650 (1996).
M. Sainio, et al., "Presymptomatic DNA and MRI diagnosis of neurofibromatosis 2 with mild clinical course in an extended pedigree," *Neurology*, 45, pp. 1314–1322 (1955).
J. Sainz, et al., "Loss of Alleles in Vestibular Schwanomas," *Archives of Otolaryngology–Head & Neck Surgery*, 119, pp. 1285–1288 (1993).

* cited by examiner

*Primary Examiner*—James Ketter
*Assistant Examiner*—William Sandals
(74) *Attorney, Agent, or Firm*—Fish & Neave; Jesse J. Jenner; Jane T. Gunnison

(57) ABSTRACT

The invention concerns a method for the determination of data for the preparation of presymptomatic or prenatal diagnosis of phakomatosis, in particular, a tumor suppressor gene disease, in a high-risk patient, in particular of neurofibromatosis, comprising the steps of: making available the tumor material from a person afflicted with the tumor suppressor gene disease, who is a relative of the high-risk patient; isolating tumor DNA from the tumor in the relative; isolating blood DNA from the blood of the relative; amplifying polymorphous DNA microsatellite markers from the tumor and the blood; separating the markers by length; observing the lengths of the markers; comparing the markers from the blood and the tumor; examining for a loss of alleles; optionally, comparing amplified markers from a second tumor of the relative; and amplifying polymorphous DNA microsatellite markers from the blood of an offspring and separating and observing the markers.

16 Claims, 2 Drawing Sheets

METHOD FOR THE DETERMINATION OF DATA FOR THE PREPARATION OF THE DIAGNOSIS OF PHAKOMATOSIS

FIELD OF THE INVENTION

The invention concerns a method for the determination of data for the preparation of the presymptomatic or prenatal diagnosis of phakomatosis, in particular of tumor suppressor gene diseases, in particular of neurofibromatosis (type 1, type 2). Such methods are useful for children of parents suffering from a hereditary disease or their grandchildren to increase the probability of early detection of a new occurrence of the hereditary disease, or (if possible) of prenatal evaluation.

BACKGROUND OF THE INVENTION

The current state of the art for the preparation of the corresponding diagnosis, for this purpose, uses a mutation analysis of the DNA section coding for the characterizing gene for the hereditary disease. These tumor suppressor gene diseases include the autosomal dominant inherited neurofibromatoses.

Neurofibromatosis occurs in two types, the peripheral type, called type 1, which represents approximately 85% of the cases, and the "central type," called type 2, which represents approximately 15% of the cases. Type 1 occurs with an incidence of approximately 1:3000, whereas type 2 occurs with an incidence of approximately 1:35,000. For descriptions of the clinical picture, reference is made to appropriate specialized medical books.

The drawback of the mutation analysis is that it is very time consuming. For example, the neurofibromtosis type 1 gene on chromosome 17 (NF1 gene) has 60 exons. A complete analysis of this gene using the known mutation analysis takes more than four months. Although the neurofibromatosis type 2 gene (NF2 gene) located on chromosome 22 is smaller, having only 17 exons, a complete analysis still takes more than one month. In addition, one drawback of the known mutation analysis is that in high-risk individuals the diagnosis can only be considered to have been confirmed by molecular genetic means if a mutation is found in the afflicted individual.

SUMMARY OF THE INVENTION

A problem of the present invention is to improve a method of the type mentioned in the introduction. The problem is solved according to the invention by means of a method according to the claims.

An advantage of the method according to the invention, in particular, is that it can be carried out very quickly. Thus, in all cases, the method according to the invention can be carried out in less than 2 weeks; moreover, if the procedure is accelerated, it can be carried out in approximately two days. The rapidity of the method according to the invention is particularly important in prenatal diagnosis. Moreover, the method according to the invention is also considerably more cost effective because of its simplicity than the mutation analysis known from the state of the art.

The method according to the invention is particularly advantageous in cases where the known mutation analysis was unable to detect any mutation in individuals who were carriers of a mutation. The method according to the invention now offers the only possibility, in sporadic cases, of ruling out, or confirming, neurofibromatosis of type 1 or 2 on a molecular basis. In this context, the exclusion of neurofibromatosis is of particular importance because, statistically, it is possible to rule out the disease in approximately 50% of the high-risk individuals. As a result, the invention not only allows the elimination of the cost-intensive mutation analyses and examinations, it also makes it possible to prevent the anxiety an individual undergoing the examination may have concerning the possibility of having inherited the disease. In addition, expensive clinical examinations are also not necessary.

In a preferred embodiment, the markers are relatively short gene-flanking or intragenic DNA sections (to 300 bp). This offers the advantage that material that may be available, for example in the form of paraffin blocks prepared after surgical interventions on skin tumors in cases with neurofibromatosis, can be used, because it is possible to amplify short DNA sections from most of the available paraffin blocks. A special advantage can be seen in the fact that, particularly in the case of neurofibromatosis, the tumor material can easily be collected by external interventions.

In an additional preferred embodiment, at least four different markers are amplified. In this manner an improved data base which prevents possible detrimental misjudgments can be created for later diagnosis.

In an additional advantageous embodiment of the invention, the diagnosis of neurofibromatosis of type 1 is prepared. For this purpose, at least one polymorphous microsatellite marker from intron 27 of the NF1 gene. Furthermore, it is preferred to use at least one additional polymorphous microsatellite marker from intron 38 of the NF1 gene. Optimal results can be achieved when a total of three or four markers from the introns mentioned are used. This is advantageous because it has been shown that, in a predominant number of the high-risk patients examined, at least one of the markers mentioned is informative. A marker is informative for a given individual if the corresponding marker is present in polymorphous form and having two different lengths on both copies of the heritable material. The markers mentioned thus guarantee that there are two peaks in the graphic representation of the markers based on the difference in length.

As the preparative step for the diagnosis, the physician can compare the two peaks of the graphic representation of the markers from the blood of the afflicted individual, first with the result of the graphic plotting of the length of the DNA microsatellite markers from the tumor, in order to establish the presence of LOH (loss of heterozygosity= LOH). Here the invention includes the knowledge that the neurofibromas of the individuals from which the tumor material was removed present a 30% loss of heterozygosity, in the case of the neurofibromatosis type 1. In the case of tumors associated with neurofibromatosis type 2, the LOH rate is even higher. Thus, based on the fact that NF1 patients present many neurofibromas, the probability is very high that LOH occurs in any of the neurofibromas of the patient, and thus that it is also present and can be detected in the tumor material made available. The LOH can be recognized in the graphic representation of the markers because in the tumor material only one peak or one imbalance of the two peaks of the corresponding marker can be recognized. Both findings mean that the corresponding tumor has lost an allele. After the detection of LOH, the same marker from the blood of the high-risk person is then examined.

In another embodiment of the invention, steps c), e), g), and i) of claim 4, are repeated at least once. In this manner, a loss of an allele can again be verified or confirmed. Thus support for the first result can be obtained, if in the case of LOH the loss of an allele can be confirmed in at least one of the additional examinations.

In an additional preferred embodiment such an LOH is verified, if possible, in at least one additional tumor of the afflicted individual, that is the above-mentioned steps are carried out with at least one additional tumor of the afflicted individual, if the tumor is available. In this manner the reliability of the data obtained can be further increased. This is particularly advantageous in prenatal diagnosis.

An additional embodiment example of the invention is also carried out by steps b), d), f), h) and j) of claim 4 with the blood of the parent who is not affected, if the high-risk patient is a child of both parents. In this manner it becomes possible to determine alleles that are not affected. This also leads, on the one hand, to an increase in the reliability of the data obtained, and, on the other hand, in some cases, it is indispensable in the evaluation of the data obtained for diagnosis. As an example pertaining to this, it is mentioned that it is possible that the graphical representation of the alleles of the afflicted individual shows that he/she has alleles A and B.

In the graphical representation of the alleles of the high-risk patient, that is in the case of the child of the afflicted individual, it is shown that the child also has alleles A and B. The graphical representation of the tumor material of the afflicted individual shows that allele A has been lost in the tumor material of the afflicted individual. In such a case, the data acquired would provide an unclear foundation for a correct diagnosis, because it is unclear which one of the alleles A and B originates from the afflicted individual. In this case, in the present embodiment, the blood of the parent who was not affected is examined. In this way a determination is made indicating which alleles originate from the parent who was not affected.

If, in the present case, the parent who is not affected has the allele A or C, then it is clear the allele A could only have originated from the unaffected parent. Similarly it would be clear in this example that allele B, which is probably exclusively responsible for the disease of the affected parent, was inherited by the child. In this case the child would have an increased risk of having the disease. In the case of NF2, it has been shown to be advantageous to use at least one of the markers CRYB2, D22S275, NF2CA3, D22S268, D22S430.

All the data made available and graphically processed by the method according to the invention then make it possible for the physician who is to make the final diagnosis to evaluate whether the disease can be ruled out in the high-risk patient examined. Indeed, if the examining physician then notes that the allele which was still present in the tumor (as for example in the case presented below) was not inherited from the relative, then the occurrence of the corresponding tumor suppressor gene disease can be ruled out.

In addition, even in the case where the high-risk patient has inherited the allele which remained in the tumor, the physician can make a diagnosis.

In such a case two diagnostic possibilities are revealed:
i. For example, if in such a case the grandparents of the high-risk patient already suffer from the corresponding tumor suppressor gene disease, it can be assumed that the high-risk patient also inherited the disease.
ii. However, if the disease in the affected parents occurred for the first time (sporadically), there is, on the other hand, also the possibility that mosaic formation occurred with a probability of 20–30%, so that the genetic change in the parents suffering from the tumor suppressor gene disease will be inherited with decreased probability by the high-risk patient.

The method according to the invention can be used, in particular, for the preparation of presymptomatic and prenatal diagnoses of neurofibromatosis, including NF1 and NF2 nerufibromatosis. Below, the present invention will be explained in an embodiment example with reference to the application of the method to high-risk neurofibromatosis patients.

European patent application EP 00113607, filed Jun. 27, 2000; Kluwe et al., (1998) "Mosaicism in Sporadic Neurofibromatosis 2 Patients," *Human Molecular Genetics* 7(13):2051–2055; and all other patents and publications cited herein are incorporated by reference.

Throughout the specification, the word "comprise," or variations such as "comprises" or "comprising," will be understood to imply the inclusion of a stated integer or group of integers but not the exclusion of any other integer or group of integers.

EXAMPLE 1

1. Material: Blood and Tumor Material

Figure 1:
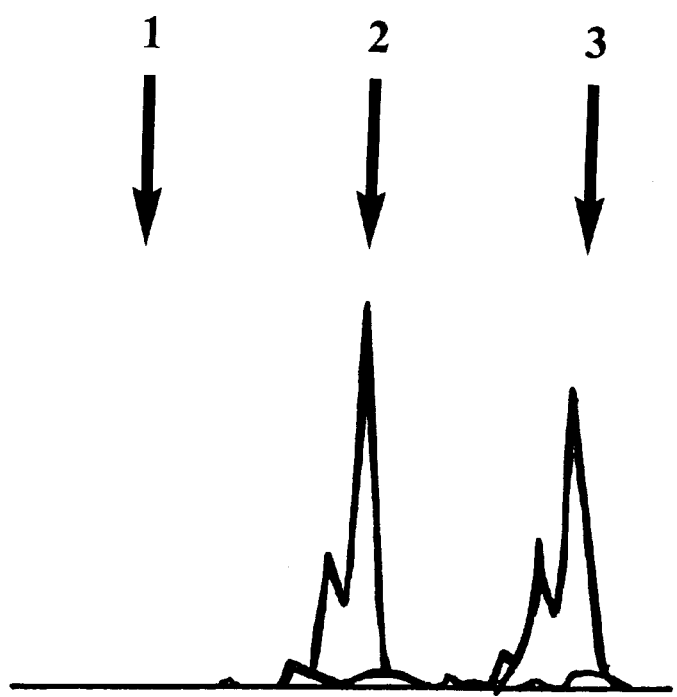
FIG. 1 is a representation of the DNA microsatellite markers separated according to their length, and amplified from the DNA of the blood of an afflicted individual.

Tumor material from a large number of patients exist in the form of paraffin blocks prepared after surgery for the disfiguring skin tumors of NF1. Tumors can be removed for cosmetic reasons at any time and without complications. In addition, tumor material exists which has been frozen and stored. All the tumors from a given patient are included in the analysis according to the invention. The above statement in principle also applies to NF2, where the material usually originates from neurosurgical and/or ETN interventions.

2. DNA Isolation

The DNA is isolated from the blood or the tumor material of the affected patient using QIAquick Blood and the QIAquick Tissue Kit from the company Qiagen. The procedure is described in the instructions for the kit provided by the company.

3. Polymorphous Markers

Four polymorphous microsatellite markers which are located in introns 27 and 38 of the NF1 gene are amplified from the blood and tumor DNA. For each patient, at least two of these four markers should be informative; otherwise an additional marker is used. In the case of NF2, different corresponding microsatellite markers are used (see above).

4. Amplification of the Markers

Using primers (oligonucleotides) having a length of approximately 20–24 bp, which flank the end of the DNA sections having variable lengths, the markers are amplified by PCR (Polymerase Chain Reaction). This amplification process is carried out or 10 $\mu$l of reaction solution, and it comprises blood or tumor DNA, oligonucleotides as primers, dNTPs, buffer, Taq polymerase and water. PCR is carried out in a thermocycler. For the following analysis, the primers are labeled with fluorescent dye.

5. Analysis of the Amplified Markers

Each of the amplified markers are mixed together. To this mixture, 0.5 ROX [6-carboxy-X-rhodamine]-length standard (ABI company) and 12 μL of demineralized formamide are added. This sample is loaded after heat denaturing onto the capillary of a Genetic Analyzer AB1310. In this separation process, the DNA sections are separated by difference in length. The results are represented graphically using the GeneScan program (company ABI). The DNA fragments are represented showing their different lengths and amounts.

6. Evaluation of the Marker Analysis

If a marker in an individual is found to be informative, there are two peaks in the graphic representation of the marker from the blood of the person. These data are compared with the results of the analysis of the tumor material. If a tumor shows only one peak pertaining to the marker, or an imbalance in the two peaks of a marker, this means that the tumor has lost an allele.

For the preparation of the diagnosis, this result can then be compared with a correspondingly prepared application of the marker from the blood of a high-risk offspring. Furthermore, the markers from the blood of the healthy parent are correspondingly prepared.

7. Results

To clarify the advantages of the invention, an example of a result of the method according to the invention is explained with reference to the attached drawing.

Figure 2:
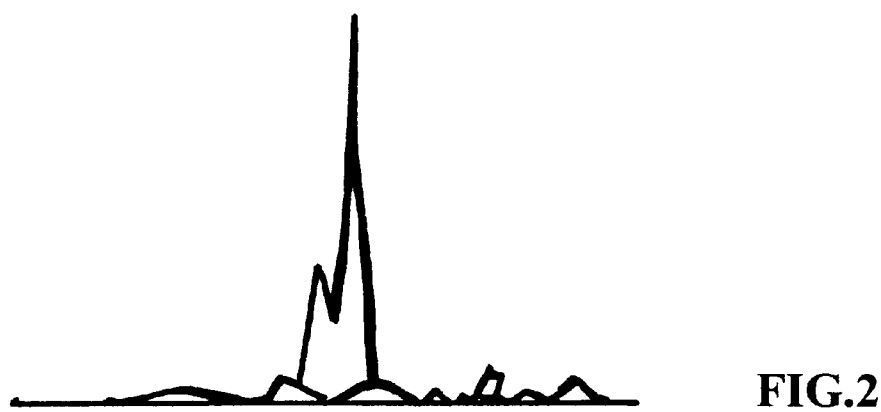
FIG. 2 is a representation of the plotting by length of the same markers as in FIG. 1, which were amplified from the tumor material of the afflicted individual.
Figure 3:
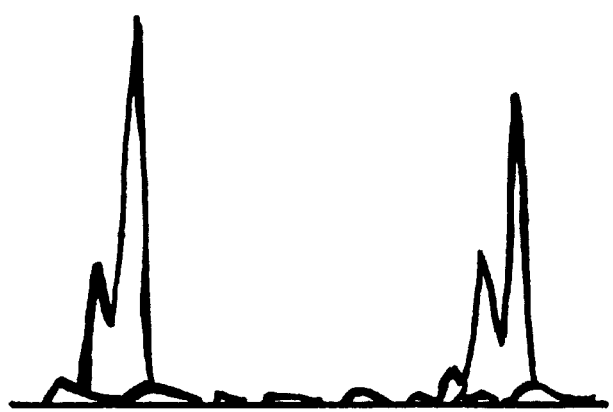
FIG. 3 is a representation of the plotting by length of the same markers which were amplified from the blood of a descendant of the afflicted individual according to FIGS. 1 and 2.

FIG. 1 is a representation of DNA microsatellite markers separated by length which were amplified from the DNA of the blood of an afflicted individual. The graphic representation represents in each case the presence of the alleles, which were called allele 2 and allele 3 in the figure. FIG. 2 is the representation of the plotting by length of the same markers as in FIG. 1, which were amplified from tumor material of the afflicted individual. One can see that the allele which was called allele 3 in FIG. 1 is lost in the tumor of the afflicted individual. FIG. 3 is a representation of the plotting by length of the same markers which were amplified from the DNA of the blood of a descendant of the afflicted individual according to FIGS. 1 and 2. FIG. 3 shows that the descendant of the afflicted individual did not inherit allele 2, which was still present in the tumor. Of alleles 2 and 3, the descendant only inherited allele 3, which was lost in the tumor. As an additional allele, the descendant also inherited allele 1 from the other parent. For the preparation of the diagnosis of the descendant, it can thus be concluded that the allele which is probably exclusively responsible for the disease was not inherited by the descendant.

Example 2

1. Patients and Methods

An afflicted individual diagnosed as having neurofibromatosis 2 (NF2) (hereinafter, "afflicted individual 358") by the updated NIH diagnostic criteria for NF2 was selected [Gutmann, D., et al., *JAMA* (1997) 278:51–57]. Biolateral vestibular schwannomas as the hallmark of NF2. One skin schwannoma was removed from afflicted individual #358.

Methods for DNA extraction from blood from individual #358 and offspring and tumor from individual #358 were performed as described in Kluwe, et al., supra. Haplotype analysis of the afflicted individual and offspring using allelic loss analysis of the NF2 gene in the tumor of the individual #358 was performed using five microsatellite markers flanking or within the NF2 gene: CRYB2, D22S275, NF2CA3, D22S268 and D22S430 [Kluwe, et al., *Neurogenet.* (2000) 3:17–24; Durham, I., et al., *Nature* (1999) 402:489–495].

2. Results

Figure 4:
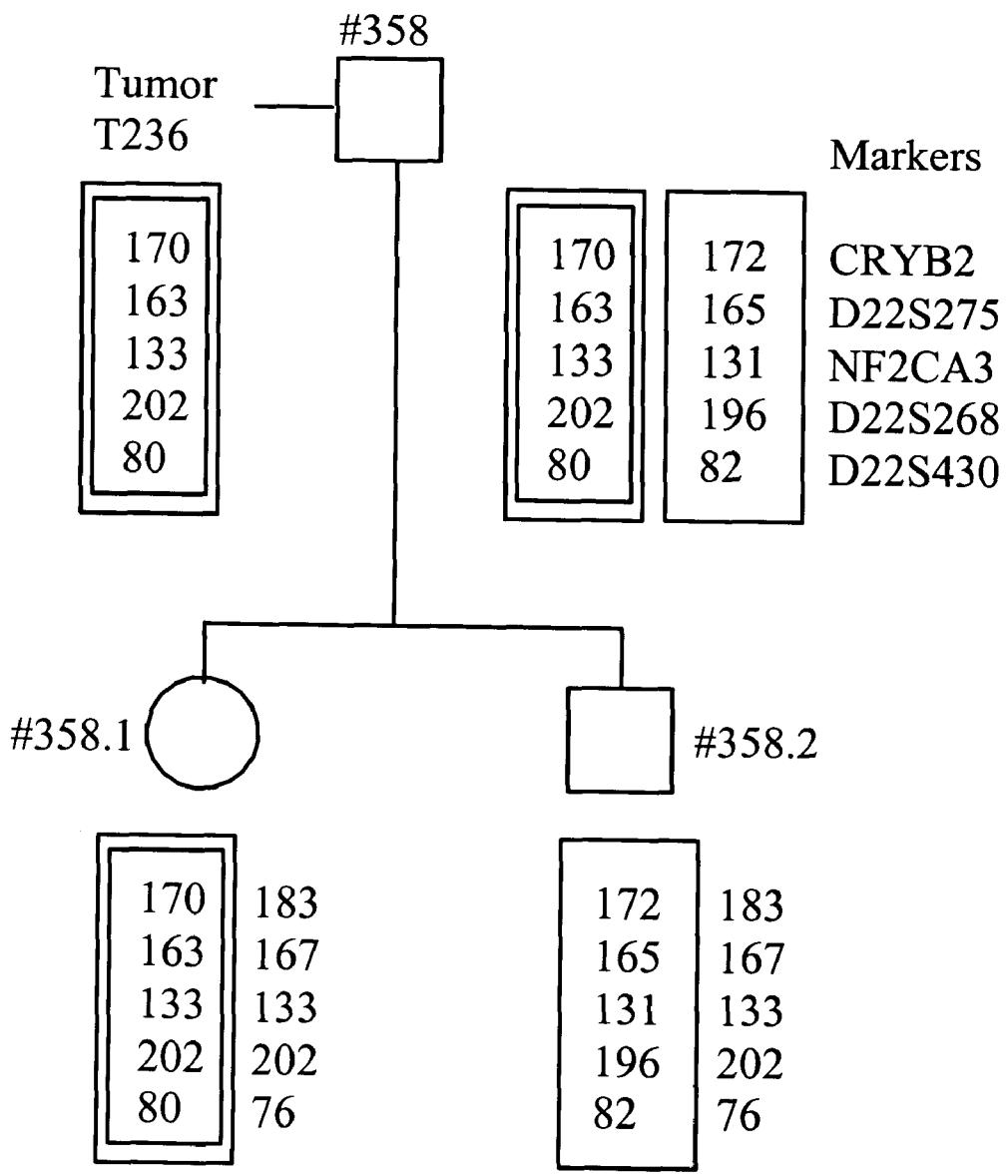
FIG. 4 is a haplotype analysis of NF2 afflicted individual #358 and offspring and LOH-analysis of the tumor.

Afflicted individual #358 had two offspring. FIG. 4 shows the haplotyping analysis for individual #358 and his two at-risk offspring as well as LOH-analysis for the tumor. The allele boxed with the single line was lost in the tumor of individual #358 and inherited by offspring #358.2. The allele boxed with double line remained in the tumor of individual #358 and beared the mutation. This allele was inherited by offspring #358.1.

I claim:

1. A method for determining whether an offspring of an individual afflicted with neurofibromatosis has an increased risk of developing neurofibromatosis comprising the steps of:

a. amplifying one or more polymorphous DNA microsatellite markers for neurofibromatosis from a tumor of the afflicted individual;

b. amplifying the one or more polymorphous DNA microsatellite markers from the blood of the afflicted individual;

c. comparing the amount and length of the one or more amplified polymorphous DNA microsatellite markers from steps (a) and (b);

d. establishing the loss of an allele (Loss of Heterozygosity) in the tumor of the afflicted individual, based on the comparison in step (c);

e. amplifying the one or more polymorphous DNA microsatellite markers from the blood of an offspring of the afflicted individual; and f. determining which allele of the afflicted individual was inherited by the offspring, wherein inheritance of the allele that is retained in the tumor of the afflicted individual indicates an increased risk of developing neurofibromatosis.

2. The method according to claim 1, wherein the one or more polymorphous DNA microsatellite markers amplified from the blood and the tumor of the afflicted individual are compared by length.

3. The method according to claim 1, wherein the offspring is not exhibiting symptoms of neurofibromatosis.

4. The method according to claim 1, wherein the offspring is a prenatal individual.

5. The method according to claim 1, further comprising the step of amplifying two or more different polymorphous DNA microsatellite markers.

6. A method for determining whether an offspring of an individual afflicted with neurofibromatosis has an increased risk of developing neurofibromatosis comprising the steps of:

a) making available tumor material of the afflicted individual, b) making available blood of the afflicted individual, c) isolating the tumor DNA from the tumor material of the afflicted individual, d) isolating the blood DNA from the blood of the afflicted individual, e) amplifying one or more polymorphous DNA microsatellite markers for neurofibromatosis genes from the tumor material, f) amplifying the one or more polymorphous DNA microsatellite markers from the blood, g) separating by amount and length the polymorphous DNA microsatellite markers from the tumor material, h) separating by amount and length the polymorphous DNA microsatellite markers from the blood, i) observing the amount and length of the polymorphous DNA microsatellite markers from the tumor material, j) observing the amount and length of the polymorphous DNA microsatellite markers from the blood, k) determining an allele that is lost in the tumor material, l) amplifying the polymorphous DNA microsatellite markers from the blood of an offspring of the afflicted individual; and m) determining which allele of the afflicted individual was inherited by the offspring based on steps (k) and (l), wherein inheritance of the allele retained in the tumor indicates an increased risk of developing neurofibromatosis.

7. The method according to claim 1 or claim 6, wherein the polymorphous DNA microsatellite marker has a length of up to approximately 300 bp.

8. The method according to claim 5 or claim 6, wherein at least three different polymorphous DNA microsatellite markers are used.

9. The method according to claim 1 or claim 6, wherein the marker is a neurofibromatosis gene flanking marker or intragenic marker.

10. The method according to claim 9, wherein at least one of the markers is located in intron 27 of the neurofibromatosis type 1 gene.

11. The method according to claim 9, wherein at least one of the markers is located in intron 38 of the neurofibromatosis type 1 gene.

12. The method according to claim 9, wherein, the marker is selected from the group consisting of CRYB2, D22S275, NF2CA3, D22S268 and D22S430.

13. The method according to claim 1 or claim 6, further comprising amplifying the one or more markers in at least one additional tumor of the afflicted individual.

14. The method according to claim 1 or claim 6, further comprising the steps of amplifying the one or more polymorphous DNA microsatellite markers from the blood of an unaffected relative of the offspring and observing the amplified marker DNA.

15. The method according to claim 6, wherein at least two different polymorphous DNA microsatellite markers are used.

16. The method according to claim 5 or claim 6, wherein at least four different polymorphous DNA microsatellite markers are used.

* * * * *